(12) United States Patent
Masuya et al.

(10) Patent No.: US 10,983,039 B2
(45) Date of Patent: Apr. 20, 2021

(54) OBSERVATION DEVICE

(71) Applicant: Hitachi High-Tech Corporation, Tokyo (JP)

(72) Inventors: Akira Masuya, Tokyo (JP); Muneo Maeshima, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 153 days.

(21) Appl. No.: 16/073,009

(22) PCT Filed: Dec. 22, 2016

(86) PCT No.: PCT/JP2016/088266
§ 371 (c)(1),
(2) Date: Jul. 26, 2018

(87) PCT Pub. No.: WO2017/130613
PCT Pub. Date: Aug. 3, 2017

(65) Prior Publication Data
US 2019/0033192 A1 Jan. 31, 2019

(30) Foreign Application Priority Data

Jan. 27, 2016 (JP) .............................. JP2016-012930

(51) Int. Cl.
*C12M 1/38* (2006.01)
*G02B 21/36* (2006.01)
(Continued)

(52) U.S. Cl.
CPC ........... *G01N 15/0227* (2013.01); *C12M 1/34* (2013.01); *C12M 1/38* (2013.01); *C12Q 1/025* (2013.01);
(Continued)

(58) Field of Classification Search
CPC ......... G06T 7/0016; G06T 7/11; G06T 7/194; G06T 2207/20021; G06T 2207/30024;
(Continued)

(56) References Cited

U.S. PATENT DOCUMENTS 7,518,652 B2 * 4/2009 Olson .................. G02B 21/002
348/351
2003/0044389 A1 * 3/2003 Brown .................... C40B 30/04
424/93.7

(Continued)

FOREIGN PATENT DOCUMENTS

JP 2007-527540 A 9/2007
JP 2009-89628 A 4/2009
(Continued)

OTHER PUBLICATIONS

German-language Office Action issued in counterpart German Application No. 11 2016 006 056.4 dated Jun. 27, 2019 with English translation (15 pages).
(Continued)

*Primary Examiner* — Nay A Maung
*Assistant Examiner* — Jose M Torres
(74) *Attorney, Agent, or Firm* — Crowell & Moring LLP

(57) ABSTRACT

In the present invention, information is analyzed, the positional relationship of cells/microbes in the optical axis direction is detected, and motility of cells/microbes is evaluated even in an out-of-focus view from an image obtained by a single image capture in an observation view of the cells/microbes. The present invention is provided with an optical system used to measure microparticles present in a sample liquid in a sample container, a drive mechanism for driving the sample container and/or a portion of the optical system in order to three-dimensionally search a bottom surface of the sample container, a control unit for controlling the
(Continued)

optical system or the drive mechanism, an image processing unit for dividing an image of microparticles in the sample container at a first time and a second time into an in-focus region and an out-of-focus region and acquiring information relating to the microparticles, and a display unit for displaying the information relating to the microparticles as information representing a temporal change between the first time and the second time.

8 Claims, 11 Drawing Sheets

(51) Int. Cl.
- *C12M 1/34* (2006.01)
- *C12Q 1/02* (2006.01)
- *G02B 21/00* (2006.01)
- *G01N 15/02* (2006.01)
- *G01N 15/14* (2006.01)
- *G06T 7/194* (2017.01)
- *G06T 7/11* (2017.01)
- *G06T 7/00* (2017.01)
- *G01N 15/00* (2006.01)

(52) U.S. Cl.
CPC ......... *G01N 15/1475* (2013.01); *G02B 21/36* (2013.01); *G02B 21/365* (2013.01); *G06T 7/0016* (2013.01); *G06T 7/11* (2017.01); *G06T 7/194* (2017.01); *G01N 2015/0003* (2013.01); *G01N 2015/0053* (2013.01); *G01N 2015/0065* (2013.01); *G01N 2015/1486* (2013.01); *G02B 21/0088* (2013.01); *G06T 2207/20021* (2013.01); *G06T 2207/30024* (2013.01)

(58) Field of Classification Search
CPC .......... G06K 9/00127; G01N 15/0227; G01N 15/1475; G01N 2015/0003; G01N 2015/0065; G01N 2015/0053; G01N 2015/1486; C12M 1/34; C12M 1/38; G02B 21/0088; G02B 21/36; G02B 21/365; C12Q 1/025
See application file for complete search history.

(56) References Cited

U.S. PATENT DOCUMENTS

| | | | |
|---|---|---|---|
| 2003/0082516 A1* | 5/2003 | Straus | G01N 33/56916 435/4 |
| 2004/0241832 A1* | 12/2004 | Muraki | C12M 41/46 435/287.1 |
| 2005/0239046 A1 | 10/2005 | Sachs et al. | |
| 2010/0328434 A1 | 12/2010 | Kiyota | |
| 2011/0069905 A1 | 3/2011 | Adiga et al. | |
| 2013/0321459 A1 | 12/2013 | Hayakawa et al. | |
| 2014/0285650 A1 | 9/2014 | Ishiwata | |
| 2015/0286887 A1* | 10/2015 | Dave | G02B 27/0025 382/275 |
| 2016/0080632 A1* | 3/2016 | Iwase | G02B 21/367 348/79 |
| 2016/0103058 A1* | 4/2016 | Glensbjerg | G01N 15/0227 382/134 |
| 2017/0160185 A1* | 6/2017 | Minemura | G01B 9/02041 |
| 2017/0309036 A1* | 10/2017 | Perraut | G01N 21/453 |
| 2017/0363533 A1* | 12/2017 | Perraut | G03H 1/0443 |

FOREIGN PATENT DOCUMENTS

| | | |
|---|---|---|
| JP | 2010-11814 A | 1/2010 |
| JP | 2011-525009 A | 9/2011 |
| JP | 2012-194168 A | 10/2012 |
| JP | 2014-209085 A | 11/2014 |
| WO | WO 2009/107321 A1 | 9/2009 |
| WO | WO 2014/094790 A1 | 6/2014 |

OTHER PUBLICATIONS

Shoa T. et al., "Extracting a Focused Image From Several Out of Focus Micromechanical Structure Images", IEEE International Conference on Acoustics, Speech, and Signal Processing, 2004, pp. 505-508, vol. 3 (four (4) pages).

Antunes M. et al., "All-in-Focus Imaging Using a Series of Images on Different Focal Planes", International Conference Image Analysis and Recognition, 2005, pp. 174-181, Springer-Verlang Berlin Heidelberg (eight (8) pages).

International Search Report (PCT/ISA/210) issued in PCT Application No. PCT/JP2016/088266 dated Apr. 11, 2017 with English translation (four (4) pages).

Japanese-language Written Opinion (PCT/ISA/237) issued in PCT Application No. PCT/JP2016/088266 dated Apr. 11, 2017 (five (5) pages).

\* cited by examiner

[FIG. 1]
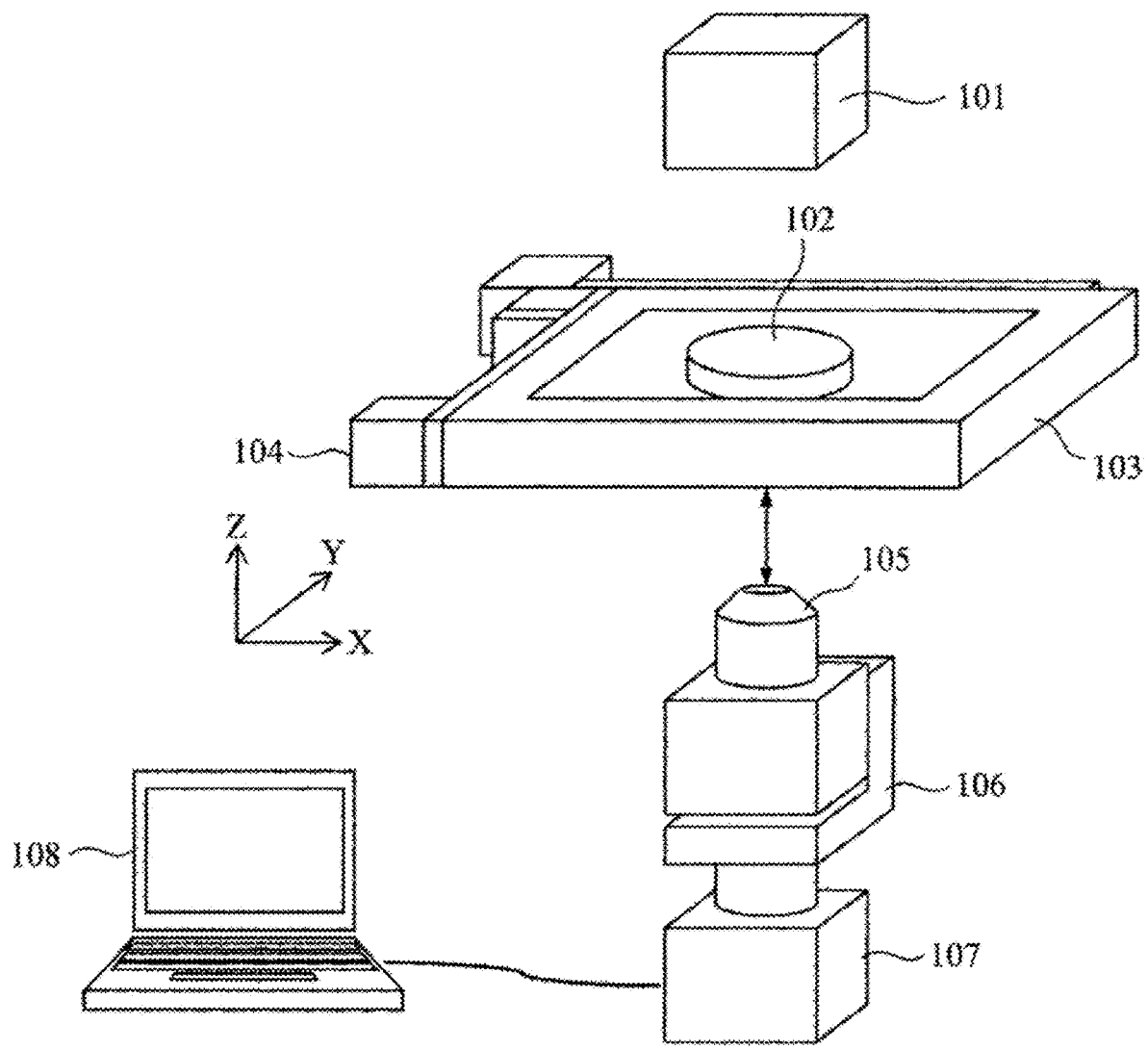

[FIG. 2]
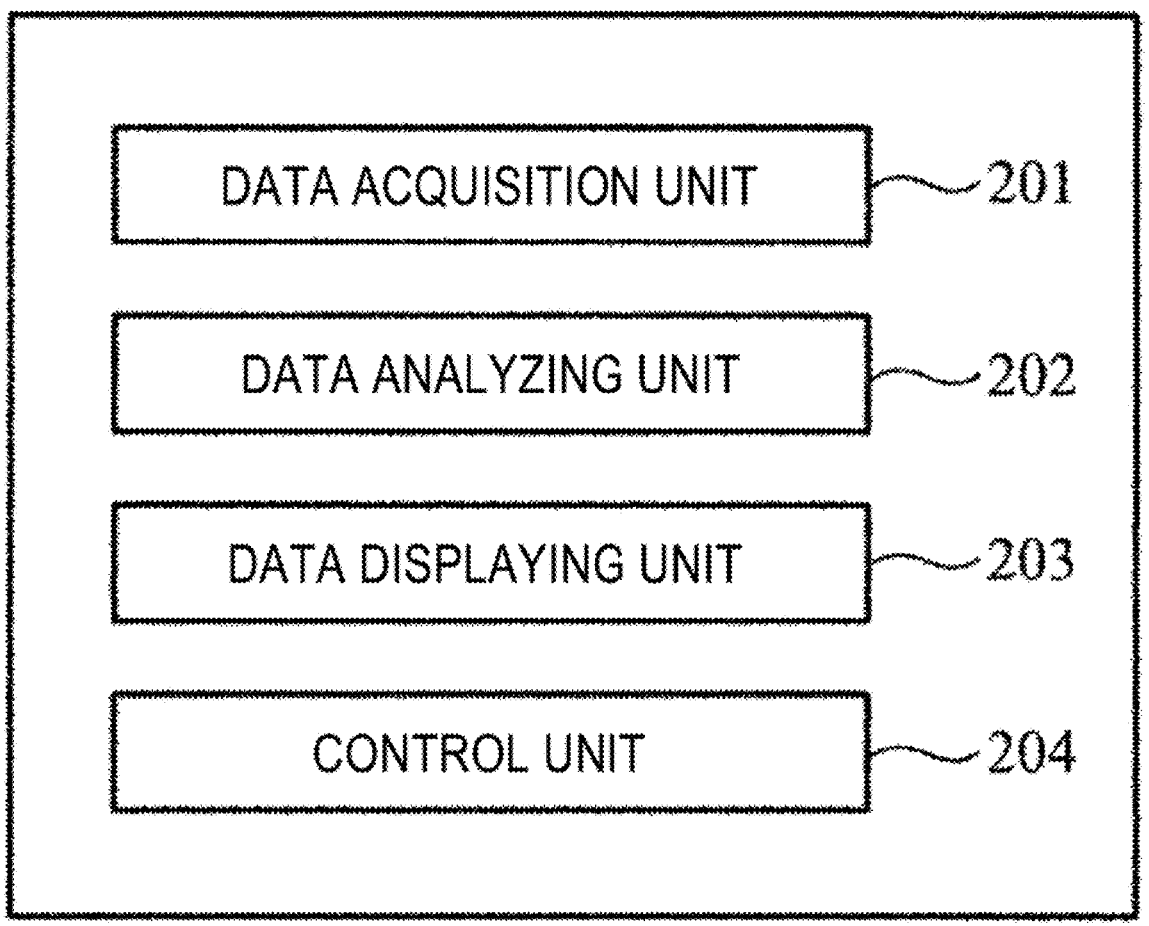

[FIG. 3A]
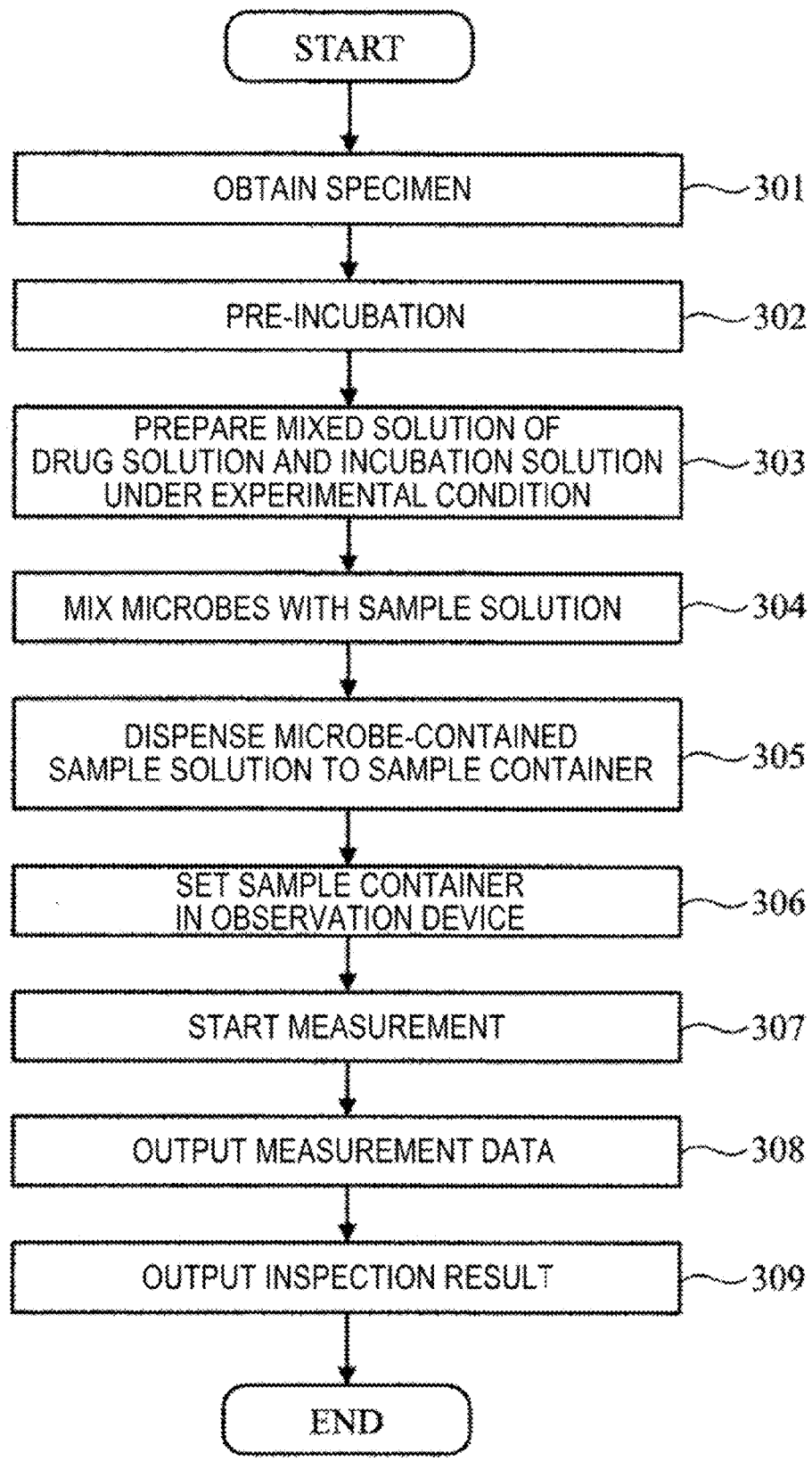

[FIG. 3B]
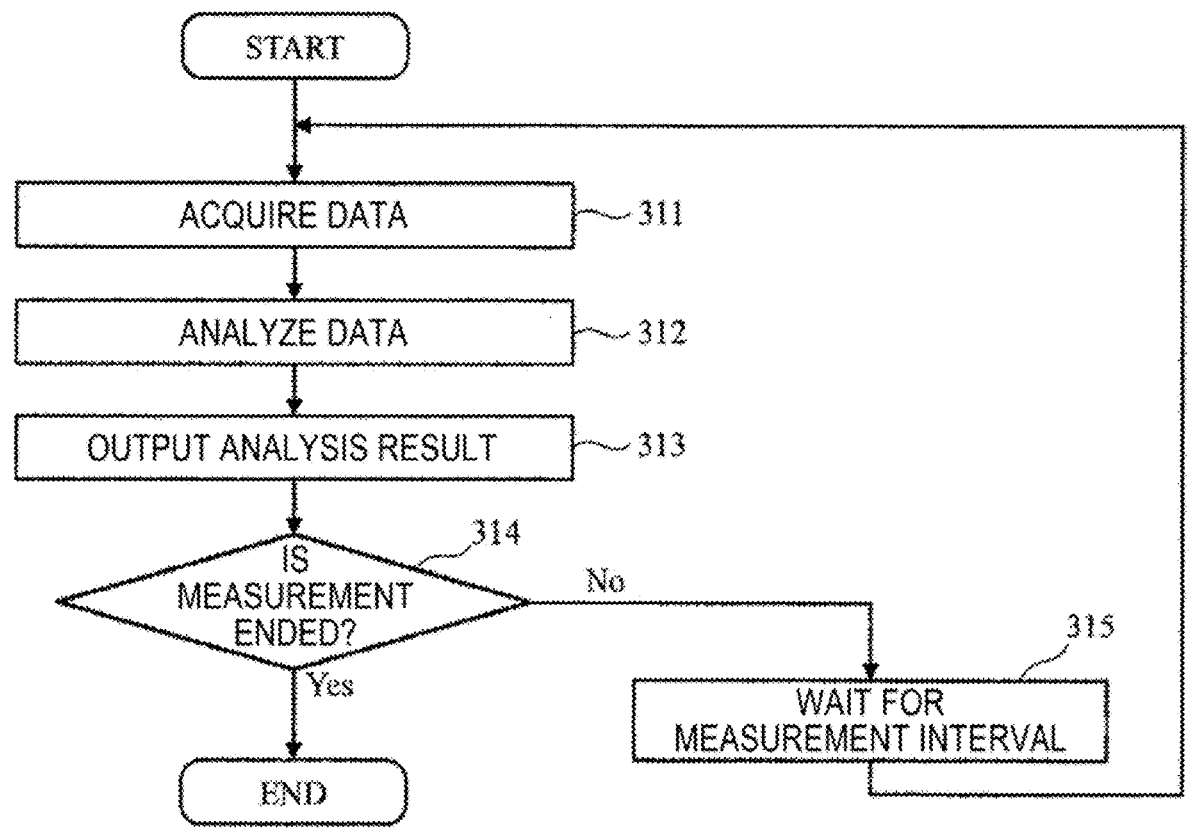

[FIG. 4A]
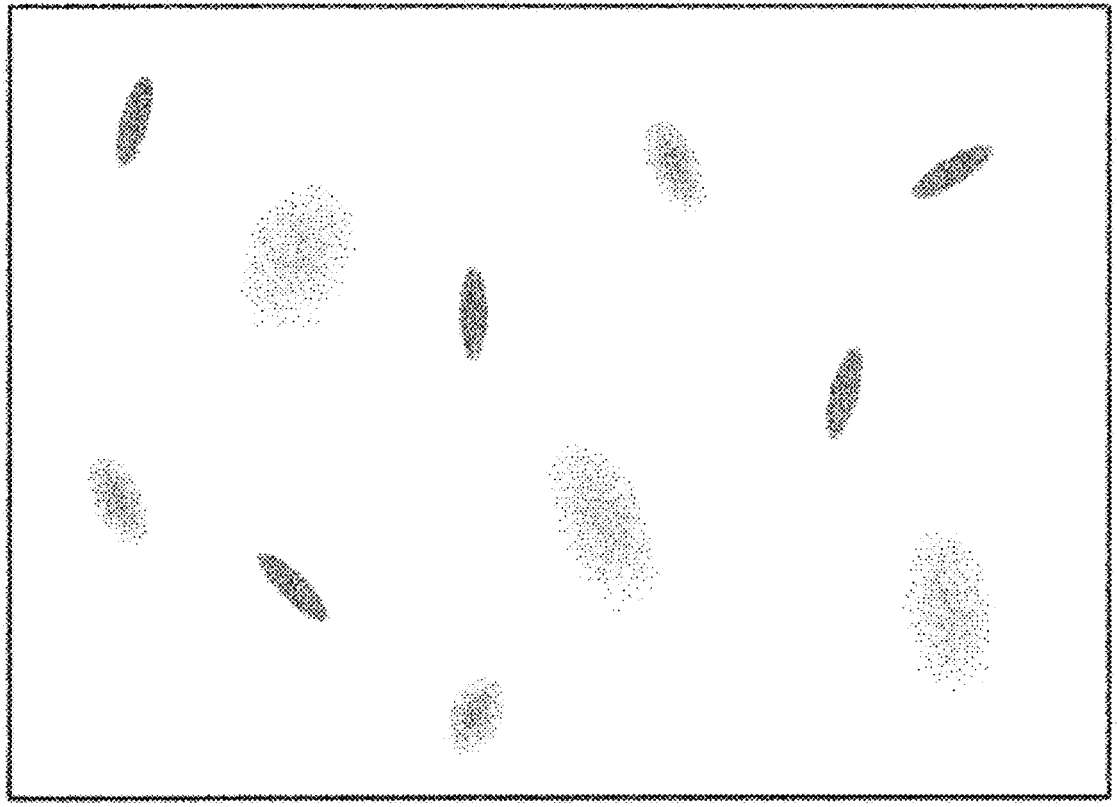
[FIG. 4B]
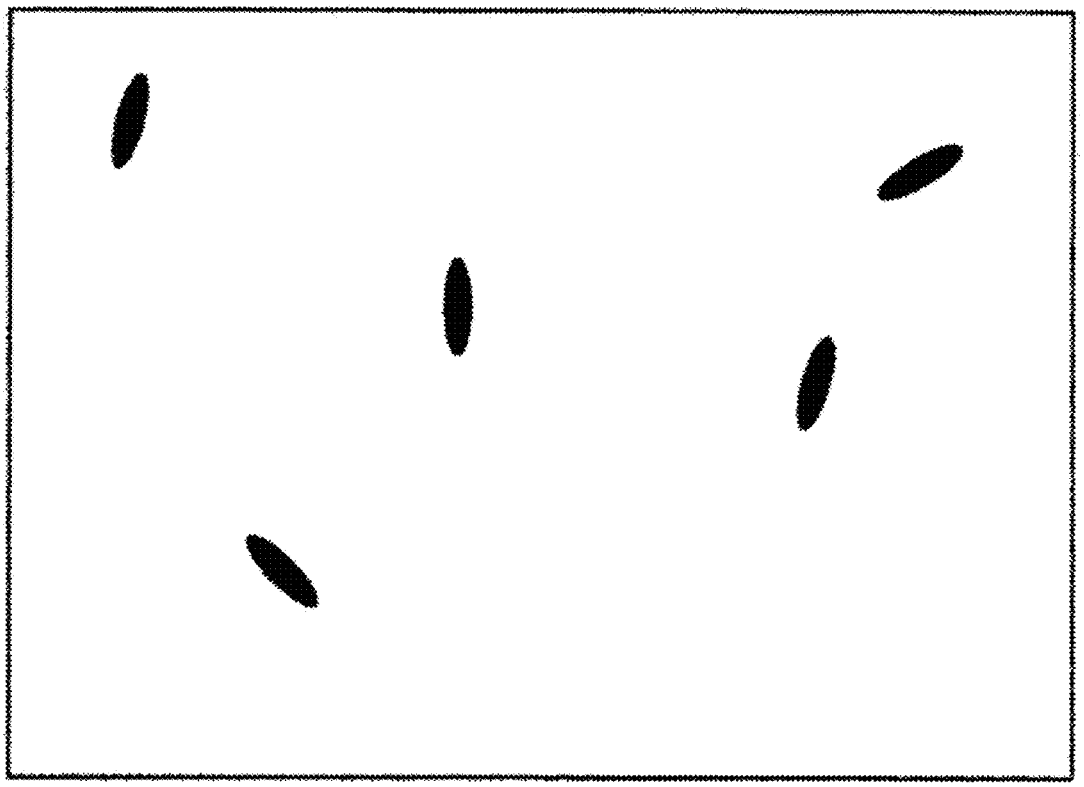

[FIG. 4C]

[FIG. 5]
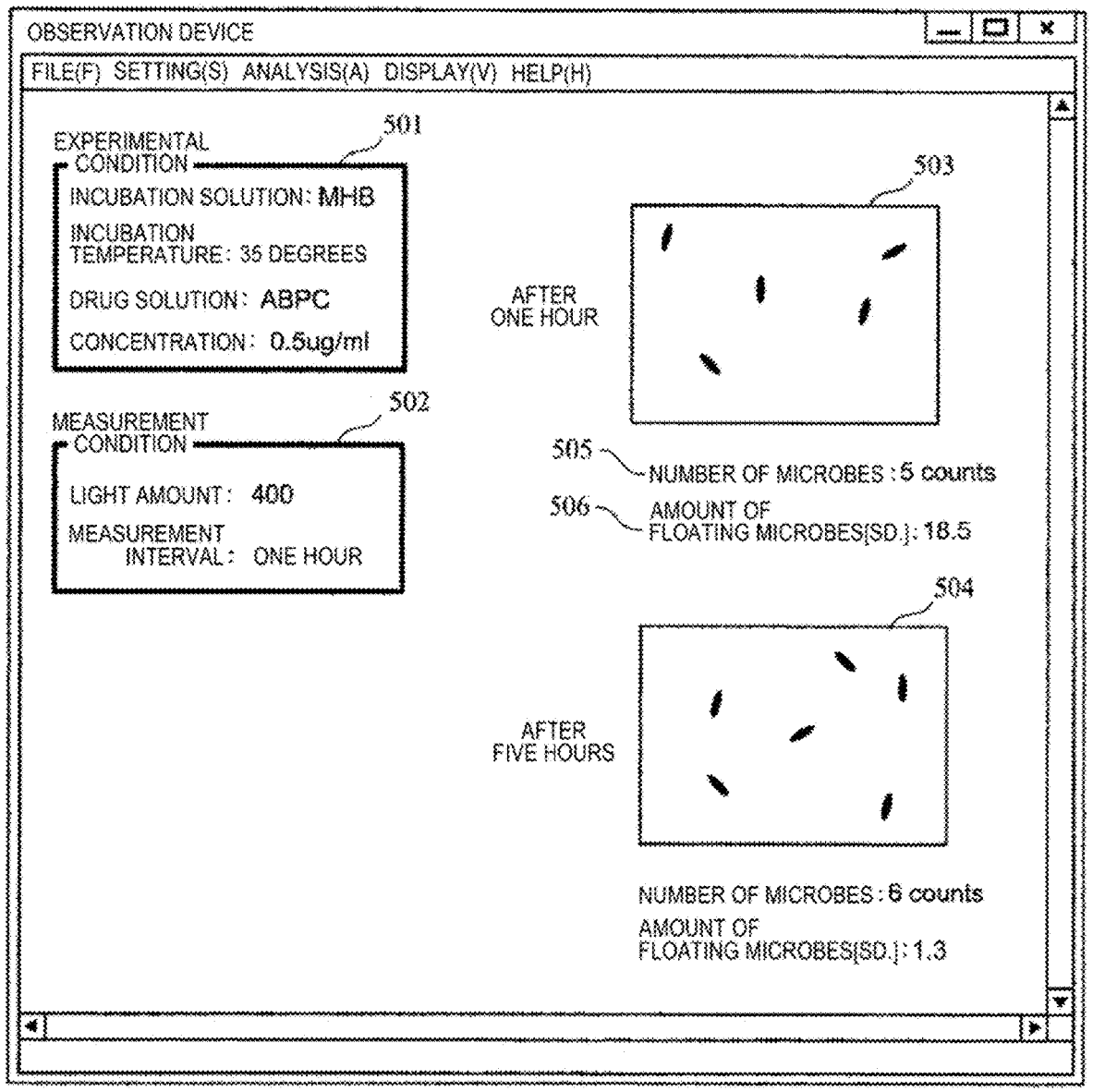

[FIG. 6A]
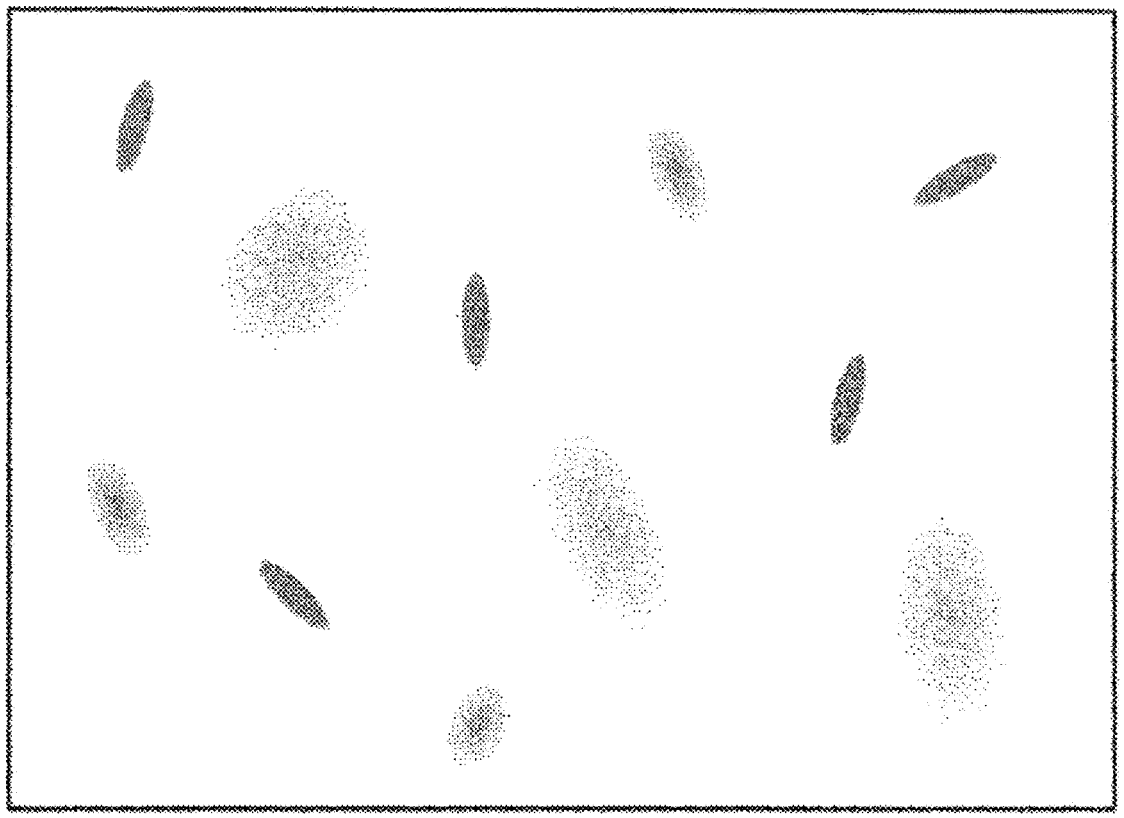
[FIG. 6B]
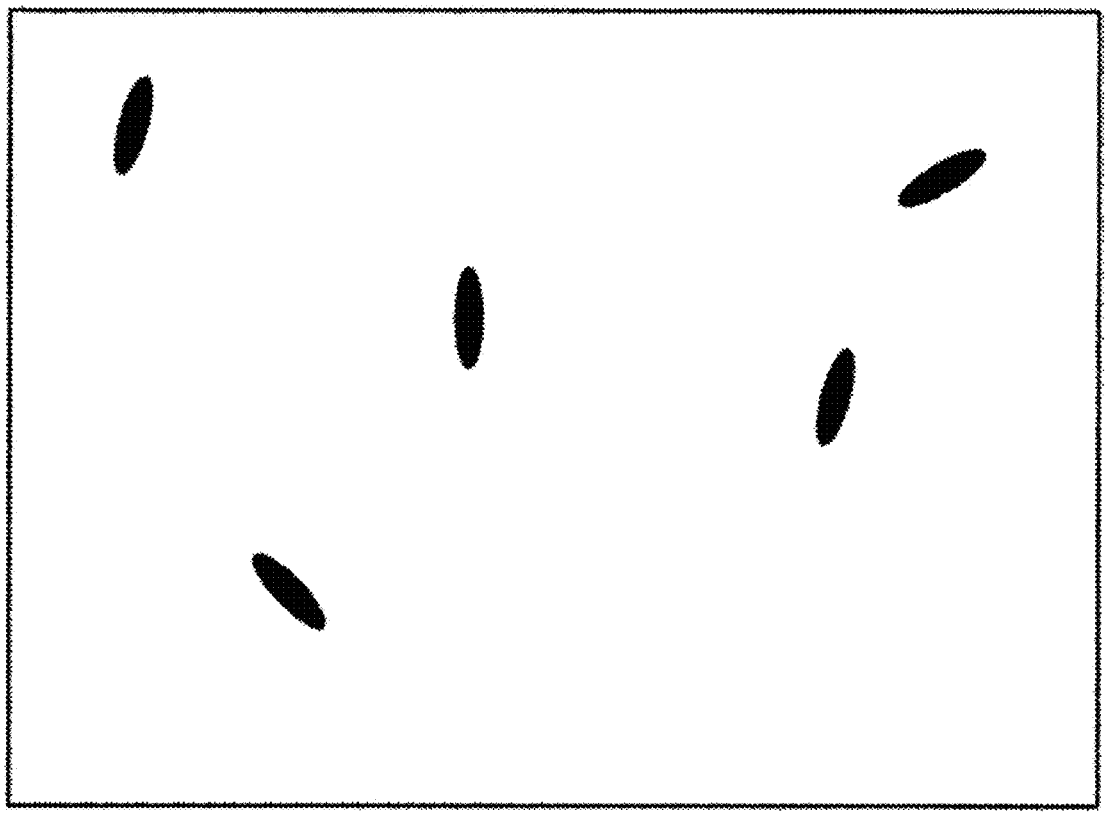

[FIG. 6C]
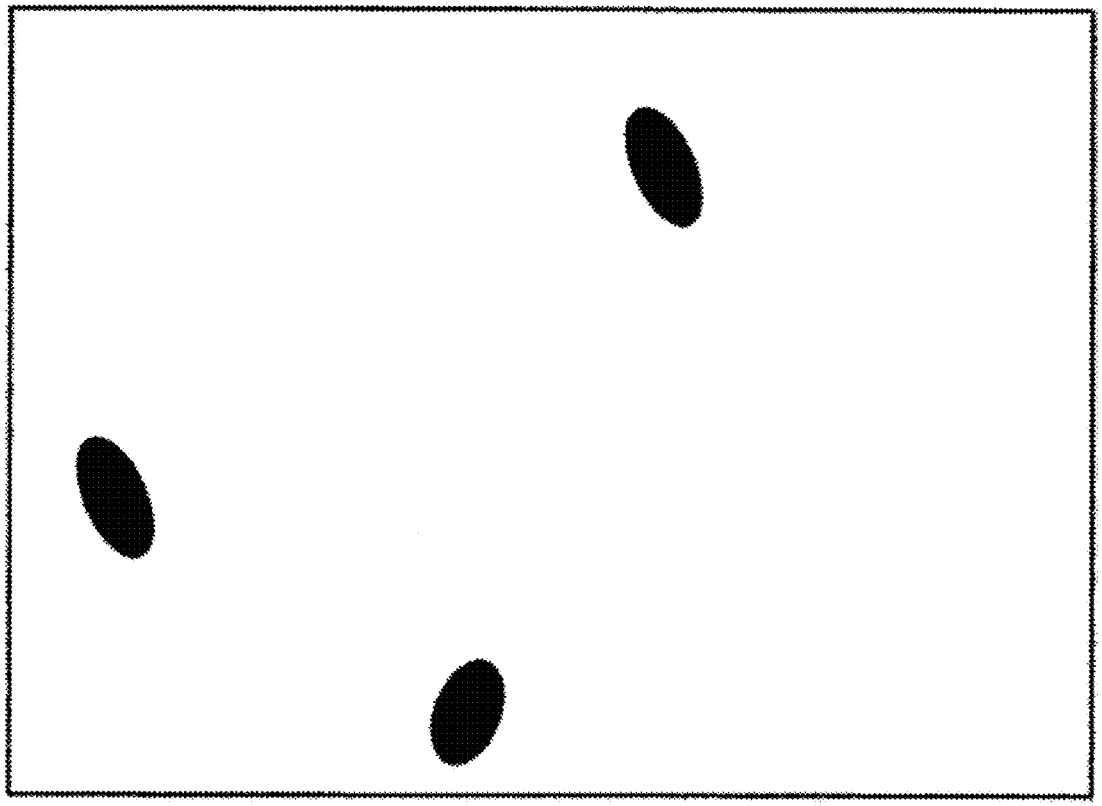
[FIG. 6D]
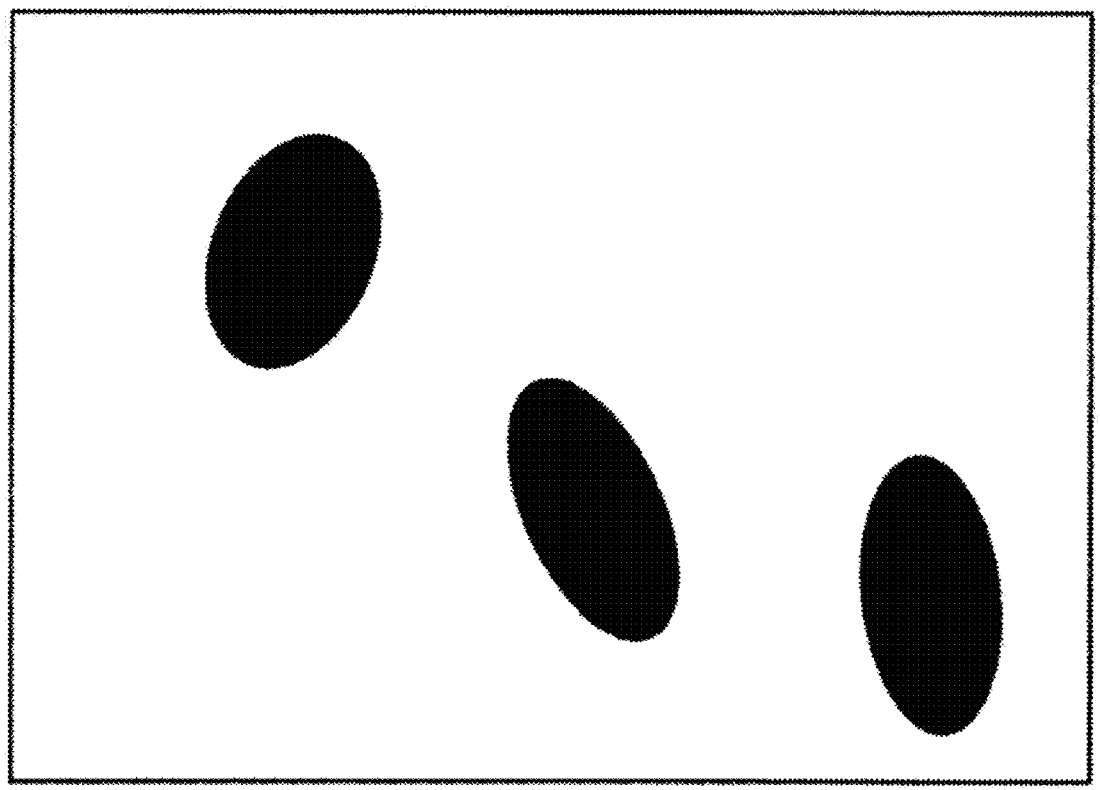

[FIG. 7]
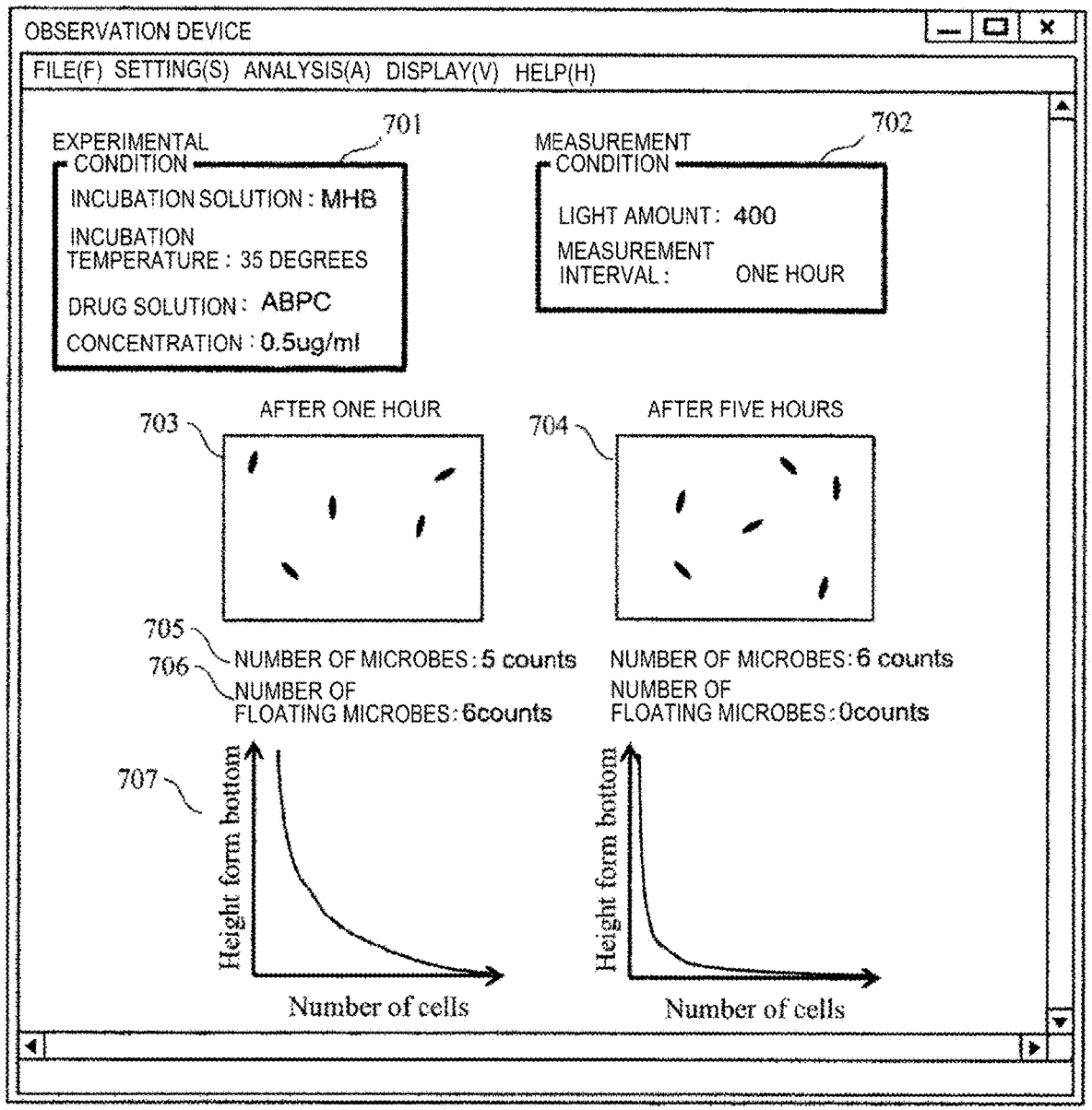

[FIG. 8]
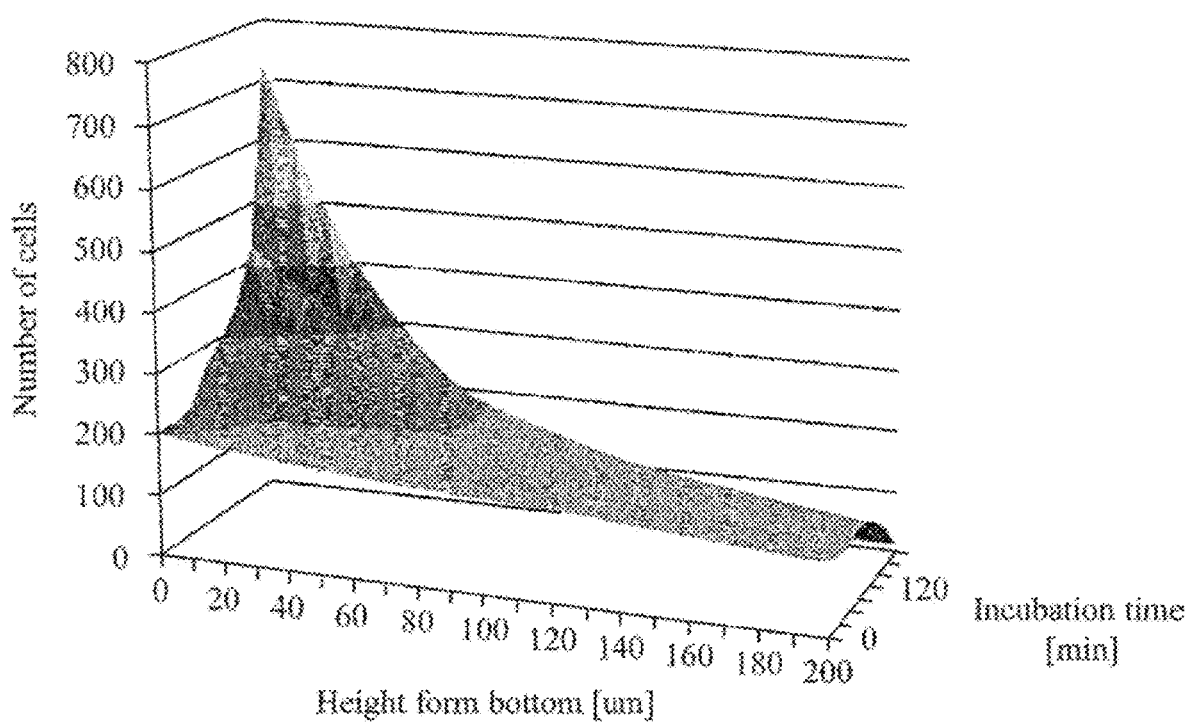

OBSERVATION DEVICE

TECHNICAL FIELD

The present invention relates to an observation device.

BACKGROUND ART

In the relate art, a measurement of an activity of a drug solution in a microorganism, cells/microbes, or the like are extensively developed in a research or clinic place in a pharmaceutical field. As a method of measuring a state of the cells/microbes in the liquid, there are mainly provided a light scattering method of analyzing the scattering of the light, and an imaging method of capturing an image by using a microscope or the like. In the light scattering method, the size or the number of particles having a relatively high concentration can be measured simply. The light scattering method is a method of measuring a scattering intensity of the light incident on a sample liquid in which the cells/microbes are suspended. The scattering intensity has a relation with the volume or the number of the cells/microbes, and is generally used as a method of inspecting the activity of the drug solution. For example, the light is radiated on the liquid in which the microbes are included, and the incident light is scattered by the microbes. The attenuation of the transmitted light is measured. Accordingly, the proliferative state of the microbes is measured. In addition, the imaging method of measuring the shape of the cells with the microscope observation as well as the volume or the number of the cells is recently used extensively. The inspection of the activity of the drug solution with respect to the cells is considered to be essential to clarify the property or the like of hepatic cells which are taken as important as a canceration mechanism or a regenerative drug solution realizing tool.

An optical microscope observation, a fluorescence microscope observation, and the like are known as a method of observing the state of the cells by imaging. Most general and simple method is the optical microscope. However, there is a case where the cells are transparent and the shape of the cells is recognized hardly. A method of observing the transparent cells by the observation method to apprehend the change of the refractive index (referred to as a phase difference observation method) is used as a method of observing the cells by an optical microscope. Compared to the typical optical microscope, the fluorescence microscope can recognize the cells with a high sensitivity by dyeing the cells with the fluorescent material. Since the fluorescence microscope necessarily dyes the cells with the fluorescent material, the cells itself as an observation target cannot be observed in some case. In addition, there is a risk that a molecule or a protein introduced as a fluorescent material affects the activity of the biomolecule. When the activity of the drug solution is inspected, it is necessary to observe the original state of the cells.

In the inspection of the activity of the drug solution with respect to the microbes, a device (sensitivity inspection device) is provided which inspects the effect of the antimicrobial on the microbes, that is, whether the proliferation of the microbes is suppressed by an antimicrobial agent. In the sensitivity inspection device, the number of the microbes is counted by using the light scattering method. As described above, the imaging method is used as a method to count the number of the microbes in addition to the light scattering method. The proliferation process of one bacterium is observed by the microscope observation. The microbes include microbes having taxis (for example, colon *bacillus*), and the change of taxis due to the antimicrobial agent can be apprehended by the imaging method. The moving image is generally acquired in order to inspect the taxis, that is, the motility. For example, as for a pulsating myocardial cell, a device is proposed which detects the effect of the drug solution on the motility (see PTL 1).

In some cases, the cells/microbes are moved to be deviated from the focal plane, so as to be positioned on the front side or the rear side of an objective lens. Although it is determined that the cells/microbes are positioned on the front side or the rear side, the motility of the cells/microbes can be evaluated. There is a device which determines whether the cells adhere to the focal plane such as the bottom surface of the sample container or are deviated from the bottom surface. It is recognized whether the cells are in the image, and it is determined whether each of the recognized cells adheres to the bottom surface of the sample container (see PTL 2).

CITATION LIST

Patent Literature

PTL 1: JP-A-2012-194168
PTL 2: JP-A-2009-89628

SUMMARY OF INVENTION

Technical Problem

In the moving image acquisition, the focal plane is fixed. Thus, in a case where the cells move in a direction to be deviated from the focal plane, the movement of the cells cannot be perceived. When the cells are deviated from the focal plane, the image of the cells is defocused and is not recognized as a cell, which has been ignored. Therefore, only the region of the cells having a clear contour is used in analyzing, and the region of the cells having an unclear contour is smoothed as a background region so that the information is removed. In addition, in order to capture a plurality of images and generate the moving image, it takes long time for a capturing time and a processing time to evaluate the motility of one sample.

In the method of determining whether each of the cells adheres to the bottom surface of the sample container, it can be perceived that the cells move in the direction to be deviated from the focal plane. However, when the cells are deviated from the focal plane, e image of the cells is defocused and is not recognized as a cell, which has been ignored. Therefore, the region of the cells having a clear contour is used in analyzing, and the information of the region of the cells having an unclear contour is not used.

In this regard, in the invention, a technique is provided by which the presence of the cells/microbes can be recognized to perform a quantitative evaluation even in a case where the cells/microbes are deviated from the focal plane and the shape thereof cannot be recognized by defocusing.

Solution to Problem

In order to solve the problems, the observation device of this application includes: an optical system which is used to measure microparticles present in a sample liquid in a sample container;

a drive mechanism which drives at least anyone of the sample container and a portion of the optical system to three-dimensionally search a bottom surface of the sample container;

a control unit which controls the optical system or the drive mechanism;

an image processing unit which divides an image of microparticles in the sample container at a first time and a second time into an in-focus region and an out-of-focus region, and acquires information relating to the microparticles; and a display unit which displays the information relating to the microparticles as information representing a temporal change between the first time and the second time.

Advantageous Effects of Invention

According to the invention, the information can be analyzed, the positional relation of cells/microbes in the optical axis direction can be detected, and the motility of cells/microbes can be evaluated even in an out-of-focus view from the image obtained by a single image capture in an observation view of the cells/microbes.

BRIEF DESCRIPTION OF DRAWINGS

FIG. 1 is a schematic view illustrating the entire system of an observation device.

FIG. 2 is a diagram for explaining various processing units of a computer.

FIG. 3A is a flowchart showing an inspection method of a microbial specimen.

FIG. 3B is a flowchart showing content of steps of the measurement data output of FIG. 3A.

FIG. 4A is a captured image which is the closest to a bottom surface of a sample container according to a first embodiment.

FIG. 4B is an image after an outline extraction of FIG. 4A according to the first embodiment.

FIG. 4C is an image of a background region of FIG. 4A according to the first embodiment.

FIG. 5 is one example of a screen which is displayed on a display of the computer according to the first embodiment.

FIG. 6A is a captured image which is the closest to a bottom surface of a sample container according to a second embodiment.

FIG. 6B is an image after an outline extraction of FIG. 6A according to the second embodiment.

FIG. 6C is an image after an outline extraction of FIG. 6A performed by a processing different from FIG. 6B according to the second embodiment.

FIG. 6D is an image after an outline extraction of FIG. 6A performed by a processing different from FIG. 6B or 6C according to the second embodiment.

FIG. 7 is one example of a screen which is displayed on a display of a computer according to the second embodiment.

FIG. 8 is another example of the screen which is displayed on the display of the computer according to the second embodiment.

DESCRIPTION OF EMBODIMENTS

This application includes a plurality of units for solving the above problem. For example, an observation device is provided which includes an optical system such as an objective lens which is used to measure cells/microbes present in a bottom surface of a sample container, a capturing element which converts an image thereof to a digital signal, and a personal computer which receives and analyzes a digital signal of the image. An image processing device has an outline extraction function that extracts a boundary line of the image having a focal point in the cells/microbes present on the bottom surface of the sample container, and a dividing function of a detection region and a background region which are divided by the boundary line thereof. The image processing device includes a detection region analyzing unit that detects the information of the cells/microbes of the detection region, a background region analyzing unit that detects the defocused microbes/cells of the background region, and a display unit that displays the analyzed information of the detection region and the background region on a monitor.

Hereinafter, the embodiments of the invention will be described with reference to the accompanying drawings. Incidentally, the accompanying drawings illustrate specific embodiments according to the principal of the invention. However, these drawings are for the purpose of understanding of the invention, and are not used for limited interpretation of the invention.

The following embodiments relate to a method or a device which inspects an activity of a drug solution of cells/microbes present in liquid including a drug solution. The following items will be described about the embodiments.
1. Outline of measurement method of observation device
2. Inspection method and result output In the following description, an XYZ orthogonal coordinate system is set. A predetermined direction in a horizontal plan is set as an X-direction, a direction orthogonal to the X-direction in the horizontal plan is set as a Y-direction, and a direction (that is, vertical direction) orthogonal to each of the X-direction and the Y-direction is set as a Z-direction.

First Embodiment

1. Outline of Measurement Method of Observation Device

FIG. 1 illustrates a schematic view of a microbes observation device of this embodiment. The microbes observation device includes, as main components, an illumination 101, a sample container 102, a pedestal 103, a XY stage 104, an objective lens 105, an objective lens actuator 106, a capturing element 107, and a computer 108.

The illumination 101 is desirably a Kohler illumination which is optically designed such that the bottom surface of the sample container 102 is lit uniformly. The sample container 102 has a storage unit which can hold at least one or more sample liquid. The pedestal 103 can hold the sample container 102, and has a structure that the light is made incident from the upper surface, and the light is discharged from the bottom surface. An XY stage 104 can move the pedestal 103 on which the sample container 102 is placed in the X-direction and the Y-direction. The XY stage 104 includes a heater (not illustrated) which performs temperature control on the sample container 102. For example, the sample container 102 may be surrounded by a transparent glass heater. In addition, the entire optical system may be surrounded by a heat insulating material, and the temperature control may be performed on the inside thereof by a heater. The objective lens actuator 106 is an actuator which moves the objective lens 105 in the Z-direction, and can scan a focal point position of the objective lens 105 in a depth direction of the sample container 102. The capturing element 107 forms the image in a focal point position of the objective lens 105. The imaging lens may be provided between the capturing element 107 and the objective lens 105. The capturing element 107 has a structure in which the image formed on the capturing element is converted into a digital signal and is transferred to the computer 108.

The computer 108 includes at least a processor such as a CPU (Central Processing Unit), a memory unit such as a memory, and a memory device such as a hard disk. In addition, the computer 108 includes an input device (such as a mouse and a keyboard) which receives the input from the user, and a display device (such as a display) which displays a measurement result.

The sample container 102 is prepared which receives the sample liquid in which the microbes and an antimicrobial to be measured is suspended. The bottom surface of the sample container 102 is desirably thin and smooth. In addition, the sample container 102 may use a microtiter plate having a plurality of sample holding units. The sample container 102 is fixed to the pedestal 103. The light having a uniform intensity is radiated from the illumination 101 on the bottom surface of the sample container 102. An image optical system such as a light field, a dark field, and a phase difference is desirable as the optical system. A light is condensed on the microbes image which is present near the lit bottom surface of the sample container 102 by the objective lens 105. The microbes image on which the light is condensed by the objective lens 105 is formed in the capturing element 107. At this time, in a case where the focal point position of the objective lens 105 does not match with the bottom surface of the sample container 102, the objective lens actuator 106 is operated to adjust a Z height position of the objective lens 105. An autofocus function which performs a process to monitor the contrast of the image captured by the capturing element 107 may be used in order to adjust the Z height position of the objective lens 105.

The image captured by the capturing element 107 is transmitted as digital data to the computer 108. The transmitted image is preserved in the storage device of the computer 108.

FIG. 2 is a diagram for explaining various processing units of the computer 108. The computer 108 controls the optical system such as a lighting 101, a drive mechanism (the objective lens actuator 106 and the XY stage 104), and the heater. The computer 108 acquires the information on the microbes at a plurality of different times. In addition, the computer 108 obtains the information which indicates the temporal change of the information on the microbes from the acquired information. In order to achieve the function, the computer 108 includes a data acquisition unit 201, a data analyzing unit 202, a data displaying unit 203, and a control unit 204.

The data acquisition unit 201 is a module which acquires the image formed by the capturing element 107. For example, the data acquisition unit 201 two-dimensionally reproduces an image from the digital data transmitted from the capturing element 107.

The data analyzing unit 202 is a module which uses the image generated in the data acquisition unit 201 as input information and outputs the analysis result of the measurement data. For example, the data analyzing unit 202 may analyze the image information at a plurality of different times, and calculate at least one quantitative value of the number of the microbes, the shape of the microbes, the size of the microbes, the amount of the floating microbes, and the occupation percentage of the microbes on the focal plane. As one example, the data analyzing unit 202 may count the number of portions having a predetermined variation value or more in the image information, and may obtain the number of the microbes. The shape of the microbes, the size of the microbes, and the occupation percentage of the microbes on the focal plane may be obtained from the size of the portions having the predetermined variation value or more in the image information.

The data analyzing unit 202 may obtain the information on the motility of the microbes from the information of the floating microbes. In addition, the data analyzing unit 202 may obtain the information on the temporal change of the motility of the microbes from the information which indicates a relation between the information of the floating microbes and the time. For example, in a case where the number of the microbes in a position separated from the bottom surface of the sample container decreases, it can be determined that the drug solution affects the microbes having taxis, and the response of the drug solution to the microbes can be detected.

As described above, the data analyzing unit 202 may include statistical software which can inspect the state change of the microbes from the temporal change of the information on the microbes.

The data displaying unit 203 is a module which displays the analysis result output from the data analyzing unit 202 on the display of the computer 108. For example, the data displaying unit 203 displays the information on the microbes in a plurality of focal planes on the display such that the temporal change can be compared.

The data displaying unit 203 may display the analysis result of the temporal change of the information on the microbes on the display. For example, the data displaying unit 203 may display the determination result about the motility of the microbes and the information on the response of the drug solution to the microbes on the display.

The control unit 204 is a module which controls each component of the microbes observation device. For example, the control unit 204 can control each component of the microbes observation device to manage the start of the measurement and the end of the measurement. In addition, when the measurement data is acquired, the control unit 204 can control the driving of the objective lens actuator 106 and the driving of the XY stage 104.

Incidentally, the processing unit described above may be operated by function of a program executed on the computer 108. In the above-described processing unit, the program code corresponding to each processing is stored in the memory. The processing unit may be operated when the process executes each program code. Incidentally, a portion of the above-described processing unit may be configured by hardware such as a dedicated circuit substrate.

2 Inspection Method and Result Output

FIG. 3A is a flowchart showing an inspection method of a microbial specimen. First, the microbes which are incubated and separated from blood or the like are obtained as a specimen (301). Since the typical amount of the microbes is small, pre-incubation is performed (302). Next, a mixed solution (sample solution) of the drug solution and the incubation solution which inspect the response to the microbes is prepared (303). The microbes are suspended in the sample solution mixed with the drug solution (304). At this time, since the response of the drug solution to the microbes requires several hours as the shortest time, a control is also prepared which is a sample solution having only an incubation solution which does not contain the drug solution. The microbe-contained sample solution is dispensed to the sample container (305). Next, the sample container is set in the observation device of this embodiment (306). The measurement of the observation device is started (307). Thereafter, while the control and the measurement are performed with respect to the temperature, the measurement data is acquired (308). The acquired measurement data is subjected to the analysis processing by the computer 108. After the analysis processing, the inspection result about the effect of the drug solution on the microbes is output on the computer 108 (309).

FIG. 3B is a flowchart showing the content of step 308 of FIG. 3A. The data acquisition unit 201 acquires the measurement data measured by the capturing element 107 (311). At this time, the control unit 204 may perform an autofocus which has a function to drive the objective lens actuator 106 and make the focal point position of the objective lens 105 match with the bottom surface of the sample container 102.

The data analyzing unit 202 analyzes two-dimensional planar data acquired in the data acquisition unit 201 (312). As one example, the data analyzing unit 202 may convert two-dimensional planar data to the image information. As another example, the data analyzing unit 202 may analyzes the image information, and calculate at least one quantitative value of the number of the microbes, the shape of the microbes, the size of the microbes, the amount of the floating microbes, and the occupation percentage of the microbes on the focal plane. In addition, the data analyzing unit 202 may measure the motility of the microbes from the calculated quantitative value. In addition, the data analyzing unit 202 may inspect the state change of the microbes from the temporal change of the information on the microbes.

The data analyzing unit 202 outputs the analysis result (313). Incidentally, at this time, the data displaying unit 203 may display the analysis result output from the data analyzing unit 202 on the display of the computer 108.

Next, it is determined whether the measurement is ended (314). In a case where the measurement is not ended, after waiting for the measurement interval (315), the procedure returns to step 311. Therefore, in this embodiment, the data analyzing unit 202 analyzes two-dimensional planar data or the image at the plurality of different times after the drug solution is put in the sample liquid. The data analyzing unit 202 can obtain the information on the response of the drug solution to the microbes from the information which indicates the temporal change of the information on the microbes. For example, after the drug solution is put in, the data analyzing unit 202 outputs the analysis result of the measurement data after one hour (first time) and the analysis result of the measurement data after five hours (second time). In step 309 of FIG. 3A performed thereafter, the data displaying unit 203 can display the analysis result of the measurement data at the first time and the analysis result of the measurement data at the second time on the display of the computer 108.

Incidentally, the data acquisition unit 201 may acquire two-dimensional planar data in the plurality of focal planes before and after the drug solution is put in the sample liquid, and the data analyzing unit 202 may obtain the information which indicates the temporal change of the information on the microbes before and after the drug solution is put in. In this case, the data analyzing unit 202 obtains the information on the response of the drug solution to the microbes from the information before and after the drug solution is put in.

FIG. 4A is one example of the acquired image. The focal point position of the objective lens 105 is in the state of matching with the bottom surface of the sample container 102. In a case where the microbes are close to the bottom surface of the sample container 102, the microbes image is not defocused, and in a case where the microbes are far from the position of the bottom surface of the sample container 102, the microbes image is defocused. FIG. 4B is an image after a processing that performs the outline extraction of FIG. 4A and binarizes the image to be divided into the region of the microbes and the background region. The outline extraction is performed using the contrast of the image. For example, a Sobel filter is generally used in the outline extraction. FIG. 4C is an image of FIG. 4A partitioned as the background region in FIG. 4B. The information of the microbes separated from the position of the bottom surface of the sample container 102 is included in the region partitioned as the background region. In a case where the defocused microbes image is included in the background region, the variation in luminance of the background region is enlarged, and a standard deviation (S.D.) is enlarged. In a case where the defocused microbes image is not included in the background region, there is only signal noise, the variation in luminance of the background region is reduced, and the standard deviation (S.D.) of the brightness is reduced. The standard deviation of the luminance of the background region has a relation with an amount of the floating microbes separated from the bottom surface of the sample container 102.

FIG. 5 is an example of the screen which is displayed on the display of the computer by the data displaying unit 203. There are provided an experimental-condition display unit 501 which displays, on the screen, the experimental condition indicating the state of the solution in which the microbes are put, a measurement condition display unit 502 which shows the incident light amount or the image measurement interval as conditions for acquiring the image, a first region 503 which displays the microbes image at the first time (for example, after one hour from the suspending of the microbes), and a second region 504 which displays the microbes image at the second time (for example, after five hours from the suspending of the microbes). Each region of the first region 503 and the second region 504 has a microbes number display unit 505 which shows the number of the microbes of the bottom surface of the sample container 102 in the image, and a floating microbes amount display unit 506 on which the standard deviation (S.D.) of the luminance of the background region indicating the amount of the floating microbes is displayed.

In the screen of this embodiment, an amount relating to the amount of the floating microbes in the incubation solution is displayed in addition to the number of the microbes which are present near the bottom surface of the sample container 102. In addition, the information on the number of the microbes at different times is displayed side by side such that the time change of the number of the microbes can be compared. Therefore, it is possible to observe the response of the drug solution to the microbes according to the time elapse.

Incidentally, in the example of FIG. 5, the information (the number of the microbes and the amount of the floating microbes) on the microbes at two different times is displayed. However, the information may be displayed in the screen such that the information on the microbes at three or more different times can be compared.

The microbes observation device of the above-described embodiments includes the optical system which measures microparticles (such as microbes and cells) present in the focal plane of the objective lens 105 in the sample liquid in the sample container 102, and the drive mechanism (the objective lens actuator 105 and the XY stage 104) which makes the focal point match with the bottom surface of the sample container 102. The measurement result (observation view) of the capturing element 107 is converted to the digital data and is transferred to the computer 108. The computer 108 converts the digital data to the image information and displays the image information on the display. Herein, the computer 108 displays the measurement result at a plurality of different times on the display. In addition, the computer 108 has a processing that divides the image into two of the region of the microbes and the background region by imaging the image information. The quantitative values such as the number, the size, and the shape of the microbes are calculated from the region of the microbes. The amount of the floating microbes is calculated from the background region. The computer 108 may measure the proliferation potency or the motility of the microbes from the quantitative value, and inspect the state change of the microparticles from the time change of the motility.

According to the above-described embodiments, the shape can be measured accurately near the bottom surface of the sample container of the microparticles (such as the cells or the microbes), and the spatial distribution information indicating that the microbes float in the sample liquid can be measured from the defocused image. The information on the motility of the microparticles can be obtained from one still image without acquiring a plurality of images and photographing a moving image. In addition, after applying the drug solution (for example, antimicrobial), the effect of the microbes on the antimicrobial can be inspected from the time change of the distribution of the number of the microbes.

In addition, the presence of the taxis of the microbes and the degree of the taxis can be measured from the spatial distribution of the microbes. In addition, the degree of the taxis of the microbes can be inspected by measuring the degree of spread of the distribution of the microbes into the liquid Second Embodiment 1 Outline of Measurement Method of Observation Device A second embodiment is similar to the first embodiment.

2 Inspection Method and Result Output

As described above, by using FIGS. 3A and 3B, the data analyzing unit 202 obtains the information on the response of the drug solution to the microbes from the information before and after the drug solution is put in.

FIG. 6A is one example of the acquired image. The focal point position of the objective lens 105 is in the state of matching with the bottom surface of the sample container 102. In a case where the microbes are close to the bottom surface of the sample container 102, the microbes image is not defocused, and in a case where the microbes are far from the position of the bottom surface of the sample container 102, the microbes image is defocused.

FIG. 6B is an image after the processing that performs the outline extraction of FIG. 6A and binarizes the image to be divided into the region of the microbes and the background region. The outline extraction is performed using the contrast of the image. For example, the Sobel filter is generally used in the outline extraction. FIG. 6C is an image after the processing that performs the outline extraction on the image of FIG. 6A partitioned as the background region of FIG. 6B in the binarization parameter differently from the image processing performed in FIG. 6B. A sharpening processing may be performed as well as the binarization parameter is changed. FIG. 6D is an image after the processing that performs the outline extraction on the image of FIG. 6A partitioned as the background region of FIG. 6B and the background region of FIG. 6C in the binarization parameter differently from the image processing performed in FIG. 6C. The sharpening processing may be performed as well as the binarization parameter is changed. In this embodiment, the binarization parameter is changed in three stages, and the outline extraction of the microbes is performed according to the defocus amount. Since the defocus amount relates to the distance from the bottom surface of the sample container 102, it is possible to calculate the amount of the microbes at the distance from the bottom surface of the sample container 102. In a case where the amount of the microbes at the distance from the bottom surface is calculated with higher resolution, the binarization parameter can be changed in more stages compared to three-stage change of the binarization parameter performed in this embodiment. In addition, since the defocused image does not reflect the shape accurately, the outline of the microbes can be desirably corrected according to the defocus amount.

FIG. 7 is an example of the screen which is displayed on the display of the computer by the data displaying unit 203. There are provided an experimental-condition display unit 701 which displays, on the screen, the experimental condition indicating the state of the solution in which the microbes are put, a measurement condition display unit 702 which shows the incident light amount or the image measurement interval as conditions for acquiring the image, a first region 703 which displays the microbes image at the first time (after one hour from the suspending of the microbes), and a second region 704 which displays the microbes image at the second time (after five hours from the suspending of the microbes). Each region of the first region 703 and the second region 704 has a microbes number display unit 705 which shows the number of the microbes of the bottom surface of the sample container 102 in the image, a floating microbes amount display unit 706 which displays the number of the floating microbes, and a microbes number distribution diagram 707 which displays the distribution of the number of the microbes at the distance from the bottom surface of the sample container 102 of the floating microbes.

In the screen of this embodiment, an amount relating to the amount of the floating microbes in the incubation solution is displayed in addition to the number of the microbes which are present near the bottom surface of the sample container 102. In addition, the information on the number of the microbes at different times is displayed side by side such that the time change of the number of the microbes can be compared. Therefore, it is possible to observe the response of the drug solution to the microbes according to the time elapse.

Incidentally, in the example of FIG. 7, the information (the number of the microbes and the amount of the floating microbes) on the microbes at two different times is displayed. However, the information may be displayed in the screen such that the information on the microbes at three or more different times can be compared.

FIG. 8 is information indicating a relation between the information of the spatial distribution of the microbes and the time. Specifically, FIG. 8 is a graph in which the temporal change of the distribution of the number of the microbes is plotted with respect to the height from the bottom surface of the sample container. In the graph of FIG. 8, a vertical axis is set as the number of the microbes, a horizontal axis is set as the height (the position in the Z-direction) from the bottom surface, and a depth axis is set as the incubation time (for example, elapsed time after the sample liquid is prepared). As one example, the data analyzing unit 202 may output the information such as FIG. 8. When the bottom surface of the sample container is set as 0 μm, the number of the microbes at the position of 0 μm increases as the time is elapsed. On the other hand, the number of the microbes at the place which is 200 μm far from the bottom surface of the sample container decreases as the time is elapsed. In a case where the microbes has taxis, the microbes tend to proliferate or be maintained at each height of the bottom surface (herein, the height of 200 μm). That the number of the microbes decreases at the place which is 200 μm far from the bottom surface of the sample container indicates that the activity of the microbes itself deteriorates since the microbes moving originally in the sample liquid lose taxis due to the effect of the drug solution (for example, antimicrobial). As described above, the effect of the antimicrobial can be inspected by analyzing the time-elapse change according to the incubation time of the distribution of the number of the microbes in the sample liquid in a height direction. Therefore, the data analyzing unit 202 may output the determination result of the response of the drug solution to the microbes from the information indicating the relation between the information of the spatial distribution of the microbes and the time.

The microbes observation device of the above-described embodiments includes the optical system which measures microparticles (such as microbes and cells) present in the focal plane of the objective lens 105 in the sample liquid in the sample container 102, and the drive mechanism (the objective lens actuator 105 and the XY stage 104) which makes the focal point match with the bottom surface of the sample container 102. The measurement result (observation view) of the capturing element 107 is converted to the digital data and is transferred to the computer 108. The computer 108 converts the digital data to the image information and displays the image information on the display. Herein, the computer 108 displays the measurement result at a plurality of different times on the display. In addition, the computer 108 has a processing that divides the image into two of the region of the microbes and the background region by imaging the image information. The quantitative values such as the number, the size, and the shape of the microbes are calculated from the region of the microbes. The amount of the floating microbes is calculated from the background region. The computer 108 may measure the proliferation potency or the motility of the microbes from the quantitative value, and inspect the state change of the microparticles from the time change of the motility. Otherwise, the gravity of the microparticles or the change of the surface state may be evaluated from the natural sedimentation of the microparticles.

According to the above-described embodiments, the shape can be measured accurately near the bottom surface of the sample container of the microparticles (such as the cells or the microbes), and the spatial distribution information indicating that the microbes float in the sample liquid can be measured from the defocused image. The information on the motility of the microparticles can be obtained from one still image without acquiring a plurality of images and photographing a moving image. In addition, after applying the drug solution (for example, antimicrobial), the effect of the microbes on the antimicrobial can be inspected from the time change of the distribution of the number of the microbes.

In addition, the presence of the taxis of the microbes and the degree of the taxis can be measured from the spatial distribution of the microbes. In addition, the degree of the taxis of the microbes can be inspected by measuring the degree of spread of the distribution of the microbes into the liquid.

REFERENCE SIGNS LIST

101: illumination
102: sample container
103: pedestal
104: XY stage
105: objective lens
106: objective lens actuator
107: capturing element
108: computer
201: data acquisition unit
202: data analyzing unit
203: data displaying unit
204: control unit
501: experimental-condition display unit
502: measurement condition display unit
503: image display unit 1
504: image display unit 2
505: microbes number display unit
506: floating microbes amount display unit
701: experimental-condition display unit
702: measurement condition display unit
703: image display unit 1
704: image display unit 2
705: microbes number display unit
706: floating microbes amount display unit
707: microbes number distribution display unit

The invention claimed is:

1. An observation device comprising:
an optical system which is used to measure microparticles present in a sample liquid in a sample container;
a drive mechanism which drives at least any one of the sample container and a portion of the optical system to three-dimensionally search a bottom surface of the sample container;
a control unit which controls the optical system or the drive mechanism;
an image processing unit which divides an image of microparticles in the sample container at a first time and a second time into an in-focus region and an out-of-focus region, and acquires information relating to the microparticles; and
a display unit which displays the information relating to the microparticles as information representing a temporal change between the first time and the second time;
wherein the image processing unit performs division into the in-focus region and the out-of-focus region by performing an outline extraction using a contrast of the image;
wherein the information representing the temporal change is information representing a relation between information of an amount of microparticles floating in the sample liquid and a time, and the information on the amount of the microparticles floating in the sample liquid is calculated with a variation in luminance of an out-of-focus region as an index.

2. The observation device according to claim 1, wherein the out-of-focus region is further partitioned into a plurality of regions according to a defocus amount, and
an image processing is performed for each of the partitioned regions, and an amount of the microparticles is calculated for each of the partitioned regions to obtain a spatial distribution of the microparticles in the sample liquid.

3. The observation device according to claim 2, wherein a defocus correction is performed for each of the regions partitioned according to the defocus amount to obtain the spatial distribution of the microparticles in the sample liquid.

4. The observation device according to claim 2, wherein the display device displays information on the spatial distribution of the microparticles at the first time and information on the spatial distribution of the microparticles at the second time.

5. The observation device according to claim 1, the information relating to the microparticles is at least one of the number of the microparticles, a size of the microparticles, a shape of the microparticles, and an occupation percentage of the microparticles on the focal plane.

6. The observation device according to claim 1, wherein the microparticles are microbes,
the observation device further includes a mechanism which performs temperature control on the sample liquid, and
the information representing the temporal change is information representing a relation between information on an amount of the microbes floating in the sample liquid and a time.

7. The observation device according to claim 6, wherein a data analyzing unit obtains information on a motility of the microbes from the information representing the temporal change.

8. The observation device according to claim 6, wherein a data analyzing unit obtains information on a response of a drug solution to the microbes from the information representing the temporal change before and after the drug solution is put in the sample liquid.

* * * * *